United States Patent [19]

Gillet

[11] Patent Number: 5,169,978

[45] Date of Patent: Dec. 8, 1992

[54] NAPHTHYLOXYBENZOIC AND NAPHTHLOXYNAPHTHOIC ACID COMPOUNDS

[75] Inventor: Jean-Philippe Gillet, Brignais, France

[73] Assignee: Société ATOCHEM, Puteaux, France

[21] Appl. No.: 808,869

[22] Filed: Dec. 16, 1991

[30] Foreign Application Priority Data

Dec. 14, 1990 [FR] France .................. 90 15668

[51] Int. Cl.$^5$ ............................................. C07C 69/00
[52] U.S. Cl. ................. 560/139; 562/466; 562/467
[58] Field of Search ............... 560/139; 562/466, 467

[56] References Cited

U.S. PATENT DOCUMENTS

| | | | |
|---|---|---|---|
| 4,578,522 | 3/1986 | Eaddy | 562/466 |
| 4,739,100 | 4/1988 | Adnan et al. | 562/467 |
| 5,041,639 | 8/1991 | Shroot et al. | 562/467 |

FOREIGN PATENT DOCUMENTS 4046757 12/1979 Japan .

*Primary Examiner*—Paul J. Killos
*Attorney, Agent, or Firm*—Burns, Doane, Swecker & Mathis

[57] ABSTRACT

Novel (naphthyloxy)benzoic/naphthoic acid compounds, polymerizable into thermotropic polymers have the formulae:

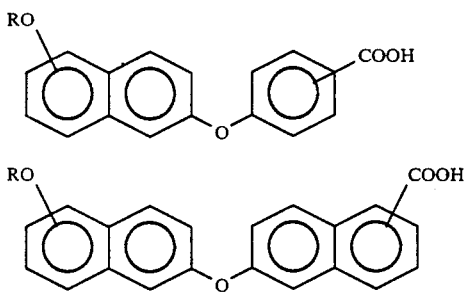

in which R is hydrogen, a straight or branched chain aliphatic or cycloaliphatic hydrocarbon radical having from 1 to 4 carbon atoms or a radical

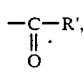

wherein R' is a methyl or ethyl radical, or salt thereof.

7 Claims, No Drawings

NAPHTHYLOXYBENZOIC AND NAPHTHLOXYNAPHTHOIC ACID COMPOUNDS

SUMMARY OF THE INVENTION

The present invention relates to novel hydroxy-, alkoxy- and acyloxynaphthyloxybenzoic and naphthyloxynaphthoic acid compounds respectively having the following formulae:

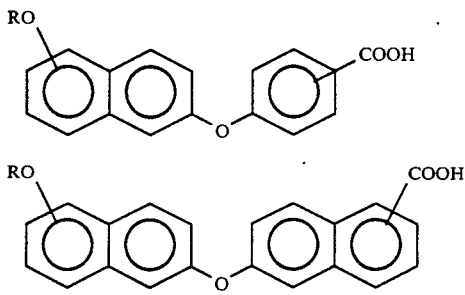

in which R is hydrogen, a straight or branched chain aliphatic or cycloaliphatic hydrocarbon radical having from 1 to 4 carbon atoms or a radical

wherein R' is a methyl or ethyl radical.

DETAILED DESCRIPTION OF THE PREFERRED EMBODIMENTS OF THE INVENTION

More particularly according to the present invention, the substituents -OR and -COOH on the napthalene and benzene rings of the above formulae may occupy any of the positions 1 to 8, albeit positions 1 and 3 are the least desirable.

Particularly exemplary of these benzoic acids are 3- and 4-(6,-methoxy-2,-naphthyloxy)benzoic acids, 3- and 4-(6'-hydroxy-2'-naphthyloxy)benzoic acids, and 3- and 4-(6,-acetoxy-2,-naphthyloxy)benzoic acids.

The (alkoxynaphthyloxy)benzoic acids may be prepared by condensing a halogenated derivative of an alkoxynaphthalene having the formula:

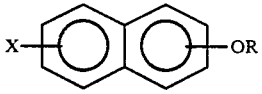

in which X is a halogen atom, preferably Cl or Br, and R is as defined above with an alkyl hydroxybenzoate of the formula:

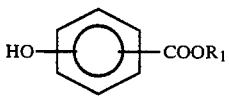

in which $R_1$ is a straight or branched chain alkyl radical having from 1 to 4 carbon atoms, preferably methyl, in the presence of a copper compound, by means of the Ullmann reaction which is well known to this art. The ester obtained is then saponified, for example using potassium hydroxide solution, such as to provide the salt of the corresponding acid, which is acidified.

To prepare the (alkoxynaphthyloxy)naphthoic acids, the same procedure is followed, but replacing the alkyl hydroxybenzoate by an alkyl hydroxynaphthoate of the formula:

The solvent used may be a diether glyme of low molecular weight, such as diethylene glycol diethyl ether. The reaction may also be carried out in the presence of a sequestering agent such as a crown ether, polyethylene glycol (diether) of high molecular weight ($\geq 1000$) or a triamine as described in EP-21,868, having the formula $N[CHR_1—CHR_2—O—(CHR_3—CHR_4—O)_n—R_5]_3$, wherein $0 \leq N \leq 10$, $R_1$, $R_2$, $R_3$ and $R_4$, which may be identical or different, are each a hydrogen atom or an alkyl radical having 1 to 4 carbon atoms and $R_5$ is a cycloalkyl, phenyl or $C_mH_{2m\phi}$ or $C_mH_{2n+1\phi}$ radical, wherein $1 \leq m \leq 12$.

The ester prepared is then saponified and the salt of the corresponding acid which is obtained is acidified.

The (hydroxynaphthyloxy)benzoic acids may be prepared from the above (alkoxynaphthyloxy)benzoic acids or their salts (it then is not necessary to carry out the final acidification step described above).

The acid or the salt is dissolved in acetic acid, which is heated to a temperature of about 120° C. before introducing HBr. The entire mass is then refluxed and stirred for several hours and allowed to cool before recovering the product which has precipitated.

When the starting material is an acid, it is preferable that the molar ratio of HBr/acid be close to 5.

When the starting material is a salt, it is necessary to carry out the reaction using an additional equivalent of HBr.

Given the poor solubility of the starting materials in acetic acid, it is desirable to conduct the operation using a large excess of acetic acid, in general on the order of 15 to 20 times the amount of starting material.

The (acetoxynaphthyloxy)benzoic acids may be synthesized from the (hydroxynaphthyloxy)benzoic acids and acid anhydride form thereof.

The reaction is preferably carried out in the presence of an excess of anhydride.

Once the mixture of the constituents has been produced, it is refluxed for about 30 min. The mixture is then cooled and diluted with water and the solids obtained are filtered off. Preferably, the solids are then recrystallized, for example from a water/acetone mixture.

The (hydroxynaphthyloxy)naphthoic and (acetoxynaphthyloxy)naphthoic acids may be synthesized in an identical manner to that used to prepare the (hydroxynaphthyloxy)benzoic and (acetoxynaphthyloxy)benzoic acids.

The naphthyloxy-substituted benzoic and naphthoic acids according to the invention may be used as monomers and, in particular, as monomers which are particularly well adopted for the synthesis of thermotropic polymers of the genera described in, for example, JP-55/133,423, JP-63/101,416 and U.S. Pat. No. 4,946,926.

In order to further illustrate the present invention and the advantages thereof, the following specific examples are given, it being understood that same are intended only as illustrative and in nowise limitative.

EXAMPLE 1

Synthesis of 4-(6'-methoxy-2'-naphthyloxy)benzoic acid:

Technique (A) The following materials were placed in a 0.25 l reactor provided with good agitation, a thermometer and a Dean and Stark apparatus:
- (i) 0.21 mol (49.8 g) of 2-bromo-6-methoxynaphthalene,
- (ii) 0.2 mol (30.4 g) of methyl parahydroxybenzoate,
- (iii) 0.2 mol (27.6 g) of potassium carbonate,
- (iv) $10^{-2}$ mol (0.63 g) of metallic copper (5% molar), and
- (v) 22 g of diethylene glycol diethyl ether.

The mixture was heated to 200° C., with stirring, using a thermostat-controlled oil bath. It was maintained at 200° C. for 1 h, 45 min. 3.6 g of liquid phase were thus distilled and 3 l of gas were evolved. The mixture was cooled to about 100° C. and transferred into a 1 l reactor and 0.3 mol of 85% potassium hydroxide in 570 cm³ of water was then added. The suspension was heated at 100° C. for 4 h. The solution was filtered in order to remove the catalyst (copper, copper oxides).

After drying, 57 g of potassium salt were obtained, the purity of which was determined as 92% by potentiometry and 94% by HPLC after acidification. The yield of product isolated was 80%. The acidification of the filtrate and of the wash water provided two additional fractions. The total yield was 84%. (B) The following materials were introduced into the same apparatus as in (A):
- (i) 0.308 mol (73 g) of 2-bromo-6-methoxynaphthalene,
- (ii) 0.28 mol (42.6 g) of methyl parahydroxybenzoate,
- (iii) 0.28 mol (38.6 g) of potassium carbonate,
- (iv) $1.4 \times 10^{-2}$ mol (0.88 g) of metallic copper,
- (v) 31 g of diethylene glycol diethyl ether, and
- (vi) 1 g of crown ether (dicyclohexano-18-crown-6)

and the synthesis was carried out under the same conditions as described under (A). The total yield of potassium salt was 89%.

Product Characteristics

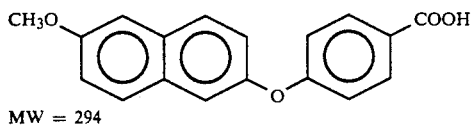

MW = 294 m.p.: 212° C. -213° C. (after recrystallization from acetic acid).

NMR: consistent structure by NMR: ¹³C and ¹H; purity > 99%

HPLC: a single peak

| | Elementary analysis: | | |
|---|---|---|---|
| | % C | % H | % O |
| Theory | 73.46 | 4.79 | 21.74 |
| Experimental | 73.31 | 4.53 | 21.41 |

EXAMPLE 2

Synthesis of 4-(6'-hydroxy-2'-naphthyloxy)benzoic acid

Technique

0/275 mol of the methoxy acid from Example 1 in the form of a salt of the acid with 5 mol (300 g) of acetic acid and then 1.39 mol (240 g) of 47% HBr were placed in a 1 l stirred reflux reactor. The acetic solution was first stirred before introducing the HBr over the course of 45 min (temperature—120° C.). Reflux was established at 116° C. The mixture was stirred under reflux for 6 h. The methyl bromide which was evolved was trapped. Upon completion of the reaction, the mixture was permitted to cool. The product which precipitated out was filtered off and washed with water. 48.5 g of product were obtained (purity by NMR: 95.3%). The filtrate was diluted with 400 cm³ of water in order to recover the dissolved product. The total yield was 78%.

Product Characteristics

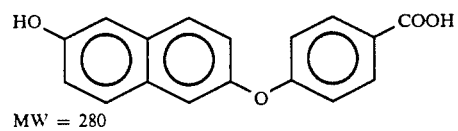

MW = 280 m.p.: 221° C. -222° C.

NRM: consistent by ¹H and ¹³C NMR purity: 99.4% after purification

HPLC: a single peak

EXAMPLE 3

Synthesis of 4-(6'-acetoxy-2'-naphthyloxy) benzoic acid

Technique 20 mmol of the hydroxy acid from Example 2 in mmol (7.5 g) of acetic anhydride were placed in a 100 cm³ stirred reactor equipped for reflux. The entire mass was heated at 136° C. for 30 min. The mixture was cooled and diluted with water and the solids were then filtered off. 3.2 g were thus recovered after recrystallization from an acetone/water mixture. The HPLC purity was 99%.

Product Characteristics

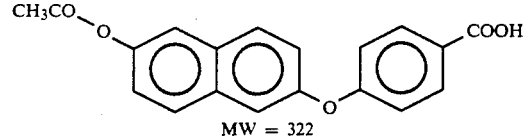

MW = 322 m.p. 200° C.

NMR: consistent by ¹H and ¹³C NMR

HPLC: a single peak

EXAMPLE 4

Synthesis of 3-(6'-methoxy-2'-naphthyloxy)benzoic acid

Technique

The following materials were placed in a reactor provided with good agitation, a thermometer and a Dean and Stark apparatus:
- (i) 0.208 mol (49.3 g) of 2-bromo-6-methoxynaphthalene,
- (ii) 0.19 mol (29 g) of methyl metahydroxybenzoate, (iii) 0.19 mol (26.2 g) of potassium carbonate,
(iv) 0.6 g of metallic copper, and
(v) 21.5 g of diethylene glycol diethyl ether.

The mixture was heated at 200° C., with stirring, for 45 min. An additional 60 g of glyme were then added. The mixture was cooled after a reaction time of 2 h, 30 min. 2.9 l of gas had evolved and a 2.6 g liquid fraction had distilled. The product was saponified by introducing 29 g of 85% potassium hydroxide in 750 g of water at 100° C. The reaction required 4 h at 100° C. The reaction mixture was filtered hot in order to remove the copper. The salt remained in solution when the mixture was cold. It was then acidified with 12 N HCl (35 cm³). The precipitate was filtered off, washed and dried: (43.7 g).

NMR purity: 97%—yield: 83.7%

It was noted that the solubility of the salt obtained was greater than that of the salt from Example 1.

Product Characteristics

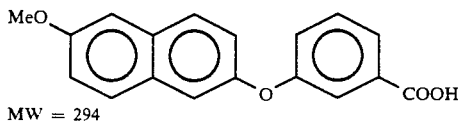

m.p.: 173° C.
NMR: consistent With the structure by ¹H and ¹³C NMR purity: 97%
potentiometric determination: 97.2%
HPLC: compatible with the system used.

EXAMPLE 5

Synthesis of 3-(6-hydroxy-2'-naphthyloxy)benzoic acid

Technique 0.135 mol (41 g) of the methoxy acid from Example 4 in 120 g (2 mol) of acetic acid were placed in a 0.5 l reactor equipped for reflux. 120 g (0.7 mol) of HBr were then introduced. The entire mass was heated to reflux (116° C.), with stirring, for 4 h and then 6 h. Upon completion of the reaction, as the mixture was homogenous, the compound was precipitated by adding 600 g of water. Solids were thus recovered, which were filtered off, washed and dried (6.5 g). The purity was 98%, which provided a yield of 43%.

Product Characteristics

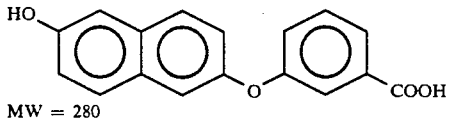

m.p.: 193° C.-195° C.
NMR: consistent by ¹H and ¹³C NMR; purity: 98.8%
HPLC: a single peak purity: 98%

EXAMPLE 6

Synthesis of 3-(6'-acetoxy-2-naphthyloxy)benzoic acid

Technique 5.6 g (0.02 mol) of the compound from Example 5 were introduced with 16 g (0.156 mol) of acetic anhydride into a 100 cm³ reactor equipped for reflux. The mixture was heated at 130° C., with stirring, for 15 min. After cooling, filtering and washing the solids with water, 4.2 g of the acetylated derivative, which had a purity of 98.5%, were isolated. The non-optimized yield was 64% of isolated product.

Product Characteristics

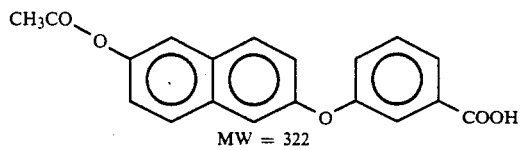

m.p.: 186° C.-187° C.
NMR: consistent structure by ¹H and ¹³C NMR; purity: 98.5%
HPLC: a single peak in the system used—purity: 99%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A benzoic/naphthoic acid compound having one of the formulae:

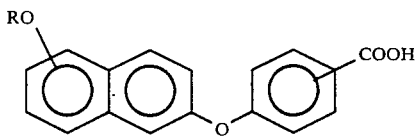

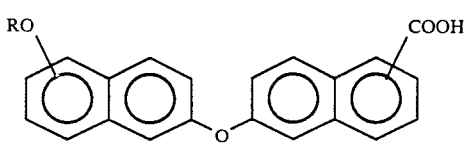

in which R is hydrogen, a straight or branched chain aliphatic or cycloaliphatic hydrocarbon radical having from 1 to 4 carbon atoms or a radical

wherein R' is a methyl or ethyl radical, or salt thereof.

2. The acid compound as defined by claim 1, the same being 3- or 4-(6'-methoxy-2'naphthyloxy)benzoic acid or salt thereof.

3. The acid compound as defined by claim 1, the same being 3- or 4-(6'-hydroxy-2'naphthyloxy)benzoic acid or salt thereof.

4. The acid compound as defined by claim 1, the same being 3- or 4-(6'-acetoxy-2'naphthyloxy)benzoic acid or salt thereof.

5. The acid compound as defined by claim 1, the same being a naphthyloxybenzoic acid derivative.

6. The acid compound as defined by claim 1, the same being a naphthyloxynaphthoic acid derivative.

7. A thermatropic polymer comprising the polymerizate of the benzoic/naphthoic acid compound as defined by claim 1.

* * * * *